US007473557B2

(12) United States Patent
Economides et al.

(10) Patent No.: US 7,473,557 B2
(45) Date of Patent: Jan. 6, 2009

(54) METHOD FOR TARGETING TRANSCRIPTIONALLY ACTIVE LOCI

(75) Inventors: Aris N. Economides, Tarrytown, NY (US); Thomas M. DeChiara, Katonah, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 20 days.

(21) Appl. No.: 10/957,760

(22) Filed: Oct. 4, 2004

(65) Prior Publication Data
US 2005/0120401 A1 Jun. 2, 2005

Related U.S. Application Data

(63) Continuation-in-part of application No. 10/163,196, filed on Jun. 5, 2002, now abandoned.

(60) Provisional application No. 60/296,260, filed on Jun. 6, 2001.

(51) Int. Cl.
*C12N 15/00* (2006.01)
*C12N 15/87* (2006.01)

(52) U.S. Cl. ............... 435/455; 435/463; 435/462

(58) Field of Classification Search ............... 435/326, 435/455, 366, 463, 462; 536/23.1
See application file for complete search history.

(56) References Cited

U.S. PATENT DOCUMENTS

| 5,922,601 | A | 7/1999 | Baetscher et al. |
| 6,150,169 | A * | 11/2000 | Smith et al. ............... 435/455 |
| 6,461,864 | B1 | 10/2002 | Soriano |

FOREIGN PATENT DOCUMENTS

| WO | WO 99/53017 | 10/1999 |
| WO | WO 03/020743 | 3/2003 |

OTHER PUBLICATIONS

Jackson and Abbot, Ed, 2000, Oxford UNiversity Press, Mouse genetics and transgenetics, A practical approach.*
U.S. Appl. No. 60/384,004, filed May 29, 2002, Fandl et al.
Nature Genetics, Aug. 1999, vol. 22, Yang, et al., "BAC-mediated gene-dosage analysis reveals a role for *Ziprol* (*Ru49/Zfp38*) in progenitor cell proliferation in cerebellum and skin", pp. 327-335.
Nature Genetics, Jan. 1999, vol. 21, Correspondence, Soriano, P., "Generalized *lacZ* expression with the ROSA26 Cre reporter strain", pp. 70-71.
Nucleic Acids Research, 1996, vol. 24, No. 8, Kellendonk, et al., "Regulation of Cre recombinase activity by the synthetic steroid RU 486", pp. 1404-1411.
Nucleic Acid Research, 1998, vol. 16, No. 6, Schwenke, et al., "Temporally and spatially regulated somatic mutagenesis in mice", pp. 1427-1432.

Nucleic Acids Research, 2000, vol. 28, No. 6, Wallace, et al., "Preselection of integration sites imparts repeatable transgene expression", pp. 1455-1464.
Genes & Development, 1999, vol. 13, Rossant, et al., "Cre'-ating mouse mutants—a meeting review on conditional mouse genetics", pp. 142-145.
EMBO Reports, 2001, vol. 21, No. 41, Vooijs, et al., "A highly efficient ligand-regulated Cre recombinase mouse line shows that *LoxP* recombination is position dependent", pp. 292-297.
Proc. Natl. Acad. Sci. USA, 1999, vol. 96, Blau et al., "Tet B or not tet B: Advances in tetracycline-inducible gene expression", pp. 797-799.
Proc. Natl. Acad. Sci. USA, 1996, vol. 93, Shockette, et al., "Diverse strategies for tetracycline-regulated inducible gene expression", pp. 5173-5176.
Nature genetics, 1999, vol. 21, Nutt, et al., "Independent regulation of the two *Pax5* alleles during cell development", pp. 390-395.
Nature Genetics, 2000, vol. 24, Correspondence, Wiles, et al., "Establishment of a gene-trap sequence tag library to generate mutant mice from embryonic stem cells", pp. 13-14.
Nature, 2001, vol. 410, Lindsay, et al., "*Tbx1* haploinsufficiency in the DiGeorge syndrome region causes aortic arch defects in mice", pp. 97-101.
Proc. Natl. Acad. Sci. USA, 1992, vol. 89, Gossen, et al., "Tight control of gene expression in mammalian cells by tetracycline-responsive promoters", pp. 5547-5551.
The American Physiological Society, 2000, Evans, et al., "Targeting the *Hprt* locus in mice reveals differential regulation of *Tie2* gene expression in the endothelium", pp. 67-75.
Am. J. Hum. Genet., 2000, vol. 67, Schwabe, et al., "Distinct mutation in the receptor tyrosine kinase gene *ROR2* cause Brachydactyly type B", pp. 822-831.
Nat. Biotechnol., 1997, vol. 15, Yang, et al., "Homologous recombination based modification in *Escherichia coli* and germline transmission in transgenic mice of a bacterial artificial chromsome", pp. 859-865.
Gene Targeting—A Practical Approach, $2^{nd}$ Ed., 2000, Edited by Joyner, A.L., Hasty, P., et al., Chapter 1, "Gene targeting, principles and practice in mammalian cells", pp. 1-35.
Nature, 1999, vol. 345, DeChiara, et al., "A growth-deficiency phenotype in heterozygous mice carrying an insulin-like growth factor II gene disrupted by targeting", pp. 78-80.

(Continued)

*Primary Examiner*—Valarie Bertoglio
(74) *Attorney, Agent, or Firm*—Tor E. Smeland, Esq.; Ying-Zi Yang; Valeta Gregg, Esq.

(57) ABSTRACT

The present invention provides a method of achieving very high targeting efficiency by utilizing targeting vectors that utilize promoter-less selection cassettes and which are engineered to targeted into transcriptionally active loci. In particular, the invention provides a method for targeting promoter-less selection cassettes into transcriptionally active loci in stem cells or other eukaryotic cells with much greater efficiency than previously observed with other methods, thus reducing the number of drug-resistant clones to be screened or eliminating the need to screen for targeted cells altogether. The invention also encompasses the DNA targeting vectors, the targeted cells, as well as non-human organisms, especially mice, created from the targeted cells.

8 Claims, 3 Drawing Sheets

OTHER PUBLICATIONS

J. Biol. Chem., 1984, vol. 259, No. 3, Abremski, K., and Hoess, R., "Bacteriophage P1 site-specific recombination—Purification and Properties of the Cre Recombinase Protein", pp. 1509-1514.

Developmental Dynamics, 1999, vol. 215, Lau, et al., "DNA methylation pattern of a tandemly repeated *LacZ* transgene indicates that most copies are silent", pp. 126-138.

Nature genetics, 1998, vol. 18, Garrick, et al., "Repeate-induced gene silencing in mammals", pp. 56-59.

Science, 1995, vol. 268, Gossen, et al., "Transcriptional activation by tetracyclines in mammalian cells", pp. 1766-1789.

J. Biol. Chem., 1978, vol. 253(5), Thimmappaya, et al., "Nucleotide sequence of DNA template for the 3 ends of SV40 mRNA II. The sequence of the DNA fragment EcorII-F and a part of EcorII-H", pp. 1613-1618.

Science, 1978, vol. 200 (4341), Reddy, et al., "The genome of simian virus 40", pp. 494-502.

Gene, 1987, vol. 60(1), Adra, et al., "Cloning and expression of the mouse *gk-1* gene and the nucleotide sequence of its promoter", pp. 65-74.

Gene, 1982, vol. 19(3), Beck, et al., "Nucleotide sequence and exact localization of the neomycin phosphotransferase gene from transposon Tn5", pp. 327-336.

Genes Dev., 1991, vol. 5(9), Friedrich, et al., "Promoter traps in embryonic stem cells: a genetic screen to identify and mutate developmental genes in mice", pp. 1513-1523.

Mech. Dev., 1999, vol. 85(1-2), Michael, et al., "Efficient gene-specific expression of Cre recombinase in the mouse embryo by targeted insertion of a novel-IRES-Cre cassette into endogenous loci", pp. 35-47.

Philos. Trans. Soc. Lond. B. Biol. Sci., 1993, vol. 339(1288), Rossant, et al., "Genome manipulation in embryonic stem cells", pp. 207-215.

Methods Cell Biol., 1998, vol. 57, Pirity, et al., "Embryonic stem cells, creating transgenic animals", pp. 279-293.

Genes Dev., 1991, vol. 5(8), Merlino, et al., "Inactivation of a sperm motility gene by insertion of an epidermal growth factor receptor transgene whose product is overexpressed and compartmentalized during spermatogenesis", pp. 1395-1406.

Somat. Cell. Mol. Genet. 1996, vol. 22(5), Schmidt-Kastner, et al., "Genes transfected into embryonal carcinoma stem cells are both lost and inactivated at high frequency", pp. 383-392.

Bioessays, 1998, vol. 20(7), S. Henikoff, "Conspiracy of silence among repeated transgenes", pp. 532-535.

Methods Enzymol., 2000, vol. 327, Baron, et al., "Tet repressor-based system for regulated gene expression in eukaryotic cells: principle and advances", pp. 401-421.

Methods Mol. Biol., 2001, vol. 158, Nagy, et al., "Creation and use of a Cre recombinase transgenic database", pp. 95-106.

J. Med. Genet., 1994, vol. 31(7), Wilkie, et al., "A gene map of congenital malformations", pp. 507-517.

Biol. Chem., 1999, vol. 380(6), Nutt, et al., "Monallelic expression of Pax5: a paradigm for the haploinsufficiency of mammalian Pax genes?", pp. 601-611.

Proc. Natl. Acad. Sci. USA, 1997, vol. 94, Zambrowicz, et al., "Disruption of overlapping transcripts in the ROSA betageo 26 gene trap strain leads to widespread expression of beta-galactosidase in mouse embryos and hematopoietic cells", pp. 3789-3794.

Gene, 1999, vol. 227, Kolb, et al., "Insertion of a foreign gene into the beta-casein locus by Cre-mediated site-specific recombination", pp. 21-31.

Gene, 2000, vol. 249, Koch, et al., "Site-specific integration of target DNA into animal cell genomes", pp. 135-144.

Shawlot, W et al. 1998. Restricted B-galactosidase expression of a hygromycin-lacZ gene targeted in the B-actin locus and embryonic lethality of B-actin mutant mice. Transgenic Research 7: 95-103.

Vaulont, S et al. 1995. Disruption of the adenosine deaminase (ADA) gene using a dicistronic promoterless construct: production of an ADA-deficient homozygote ES cell line. Transgenic Research 4: 247-255.

Mountford, P. et al. 1994. Dicistronic targeting constructs: Reporters and modifiers of mammalian gene expression. Proc. Natl. Acad. Sci. USA 91:4303-4307.

\* cited by examiner

METHOD FOR TARGETING TRANSCRIPTIONALLY ACTIVE LOCI

CROSS-REFERENCE TO RELATED APPLICATIONS

This application is a continuation-in part of U.S. patent application Ser. No. 10/163,196, filed Jun. 5, 2002, now abandoned which claims the benefit under 35 USC § 119(e) of U.S. provisional application 60/296,260, filed 6 Jun. 2001, which applications are herein specifically incorporated by reference in their entirety.

BACKGROUND OF THE INVENTION

1. Field of the Invention

The field of this invention is a method of targeting promoter-less selection cassettes into transcriptionally active loci, for the purpose of ensuring very high efficiency of targeting compared to traditional targeting methods.

2. Description of Related Art

Transgenic and knockout (KO) animals are used extensively to gain insight into gene function and to evaluate putative drug-targets in whole organisms. In the case of KO animals, a gene of interest is usually replaced by a marker gene to create a heterozygous null allele that can then be bred to homozygocity. In spite of the advantages and utility of transgenic animal technology, currently available methods for creating transgenic animals suffer from several technological problems. Some of the more serious problems associated with this method arise from the fact that DNA constructs introduced into genomes integrate randomly and frequently in multiple copies. In turn, this random integration can often lead to subsequent problems due to positional effects, silencing of the transgene, and insertional inactivation of an endogenous allele. A need still remains for methods that allow rapid, reproducible, efficient, and simple generation of transgenic and knockout animals that are devoid of the confounding issues that exist in currently available methods.

U.S. Pat. No. 6,150,169 describes methods for obtaining expression of a heterologous gene in a host. WO 99/53017 describes methods for generating transgenic animals. Vaulont et al. (1995) Transgenic Research 4:247-255 describes the use of a dicistronic promoter-less construct. Friedrich et al. (1991) Genes Development 5:1513-1523 describes random integration of a promoter-less vector into ES cells. Zambrowicz et al. (1997) Proc. Natl. Acad. Sci. USA 94:3789-3794 characterizes the ROSA26 locus.

SUMMARY OF THE INVENTION

In a first aspect, the invention provides a method for targeting a promoter-less selection cassette into a transcriptionally active locus in eukaryotic cells, comprising:

(a) constructing a DNA targeting vector containing a nucleotide sequence, wherein the DNA targeting vector comprises a 5' homology arm, a eukaryotic promoter-less selection cassette, and a 3' homology arm, wherein the promoter-less selection cassette comprises a splice acceptor sequence, a selectable marker gene, a first polyadenylation signal sequence, and wherein the 5' and 3' homology arms are derived from the transcriptionally active locus;

(b) introducing the DNA targeting vector of (a) into eukaryotic cells;

(c) selecting the eukaryotic cells of (b) that express the selectable marker, and (d) screening the selectable marker expressing eukaryotic cells of (c) to identify those cells in which the promoter-less selection cassette has integrated by homologous recombination into the transcriptionally active locus.

In one embodiment, the eukaryotic promoter-less selection cassette is flanked by two recombinase recognition sequences. In one embodiment, the recombinase recognition sequences are site-specific recombinase recognition sequences. In one embodiment, orientations of the two recombinase recognition sequences are the same. In a specific embodiment, the site-specific recombinase recognition sequences are LoxP sites, and in the presence of Cre recombinase the eukaryotic promoter-less selectable marker gene cassette is excised.

In one embodiment, the eukaryotic promoter-less selection cassette is optionally followed by a promoter-less gene of interest and a second polyadenylation signal sequence.

In one embodiment, the eukaryotic cell is an embryonic stem (ES) cell. In a preferred embodiment, the ES cell is a mouse ES cell.

In one embodiment, the transcriptionally active locus is the ROSA26 locus.

In one embodiment, the selectable marker gene is operably linked to a prokaryotic promoter, wherein the prokaryotic promoter is silent in a eukaryotic system. In one specific embodiment, the prokaryotic promoter is an EM7 promoter. In one embodiment, the selectable marker gene is a drug resistance gene. In a specific embodiment, the drug resistance gene is a neomycin phosphotransferase gene (neo$^r$).

In a second aspect, the invention provides a method for modifying a eukaryotic cell by targeting a promoter-less selection cassette into a transcriptionally active locus in the eukaryotic cell, comprising:

(a) constructing a DNA targeting vector containing a nucleotide sequence, wherein the DNA targeting vector comprises a 5' homology arm, a eukaryotic promoter-less selection cassette, and a 3' homology arm, wherein the promoter-less selection cassette comprises a splice acceptor sequence, a selectable marker gene, a first polyadenylation signal sequence, and wherein the 5' and 3' homology arms are derived from the transcriptionally active locus;

(b) introducing the DNA targeting vector of (a) into eukaryotic cells;

(c) selecting the eukaryotic cells of (b) that express the selectable marker, and (d) screening the selectable marker expressing cells of (c) to identify those cells in which the promoter-less selection cassette has integrated by homologous recombination into the transcriptionally active locus.

In a third aspect, the invention provides a method of targeting a selection cassette into the ROSA26 locus in mouse embryonic stem cells, comprising:

a) constructing a DNA targeting vector containing a nucleotide sequence, wherein the DNA targeting vector comprises a 5' homology arm, a eukaryotic promoter-less selection cassette, and a 3' homology arm, wherein the promoter-less selection cassette comprises a splice acceptor sequence, a selectable marker gene, a first polyadenylation signal sequence, and wherein the 5' and 3' homology arms are derived from the ROSA26 locus;

b) introducing the DNA targeting vector of (a) into the mouse embryonic stem cells;

c) selecting the embryonic stem cells of (b) for expression of the selectable marker gene, and d) screening the selected embryonic stem cells of (c) to identify those cells in which the selection cassette has integrated by homologous recombination into the ROSA26 locus.

In a fourth aspect, the invention features a method of genetically modifying the ROSA26 locus in mouse embryonic stem cells, comprising:

a) constructing a DNA targeting vector containing a nucleotide sequence, wherein the DNA targeting vector comprises a 5' homology arm, a eukaryotic promoter-less selection cassette, a gene of interest, and a 3' homology arm, wherein the promoter-less selection cassette is flanked by two site-specific recombinase recognition sequences and comprises a splice acceptor sequence, a selectable marker gene, a first polyadenylation signal sequence, wherein the gene of interest comprises the desired genetic modification, and wherein the 5' and 3' homology arms are derived from the ROSA26 locus;

b) introducing the DNA targeting vector of (a) into the mouse embryonic stem cells;

c) selecting the embryonic stem cells of (b) for expression of the selectable marker gene, and d) screening the selected embryonic stem cells of (c) to identify those cells in which the selection cassette has integrated by homologous recombination into the ROSA26 locus.

In a fifth aspect, the invention provides a non-human organism containing a modified transcriptionally active locus, produced by a method comprising the steps of:

(a) constructing a DNA targeting vector containing a nucleotide sequence, wherein the DNA targeting vector comprises a 5' homology arm, a eukaryotic promoter-less selection cassette, a gene of interest, and a 3' homology arm, wherein the promoter-less selection cassette is flanked by two site-specific recombinase recognition sequences and comprises a splice acceptor sequence, a selectable marker gene, a first polyadenylation signal sequence, wherein the gene of interest comprises the desired genetic modification, and wherein the 5' and 3' homology arms are derived from the transcriptionally active locus;

(b) introducing the DNA targeting vector of (a) into eukaryotic cells;

(c) selecting the eukaryotic cells of (b) that express the selectable marker, (d) screening the selectable marker expressing cells of (c) to identify those cells in which the promoter-less selection cassette has integrated by homologous recombination into the transcriptionally active locus;

(e) introducing the eukaryotic cells of (d) into a blastocyst; and (f) introducing the blastocyst of (e) into a surrogate mother for gestation.

In specific embodiment, the modification introduced in the transcriptionally active locus comprises deletion of a coding sequence, gene segment, or regulatory element; alteration of a coding sequence, gene segment, or regulatory element; insertion of a new coding sequence, gene segment, or regulatory element; creation of a conditional allele; or replacement of a coding sequence or gene segment from one species with an homologous or orthologous coding sequence from the same or a different species, and in particular wherein the alteration of a coding sequence, gene segment, or regulatory element comprises a substitution, addition, or fusion, wherein the fusion comprises an epitope tag or bifunctional protein.

Other preferred embodiments are where the blastocyst is a mouse, rat, or other rodent blastocyst and the surrogate mother is a mouse, rat, or other rodent. In a preferred embodiment the non-human organism is a mouse.

Other objects and advantages will become apparent from a review of the ensuing detailed description.

DETAILED DESCRIPTION

Figure 1:
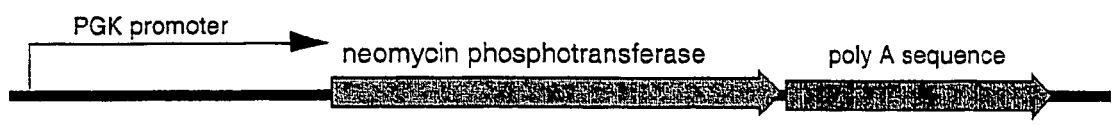
FIG. 1: A typical selection marker gene-containing cassette consists of a ubiquitously expressed promoter such as the phosphoglycerate kinase promoter (pgk), which drives the expression of a positive drug selection gene such as neomycin phosphotransferase or other suitable drug selection, followed by a polyadenylation signal sequence.
Figure 2A:
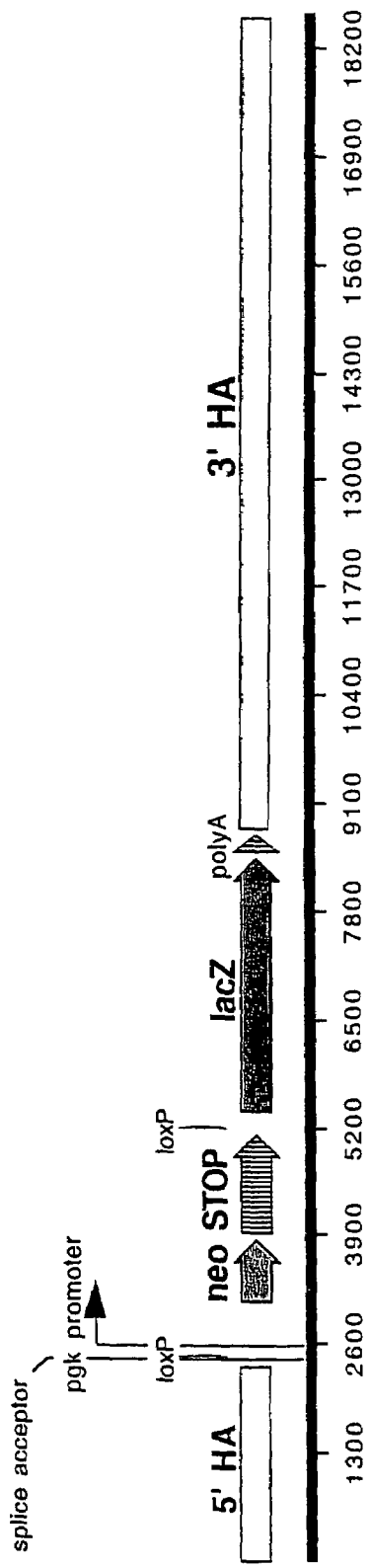
FIGS. 2A-2B: A comparison of a traditional targeting vector (FIG. 2A) and a promoter-less selection cassette-containing targeting vector (FIG. 2B).
Figure 2B:
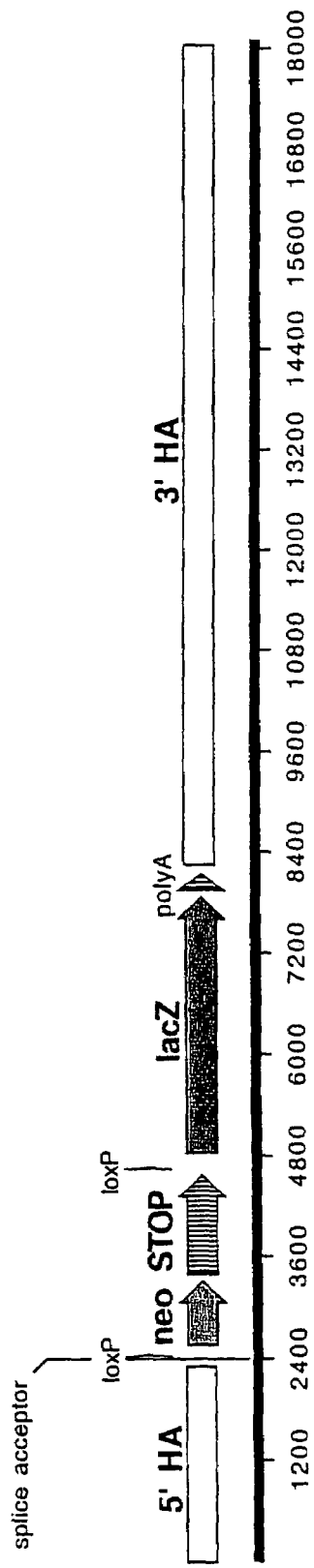
Figure 3:
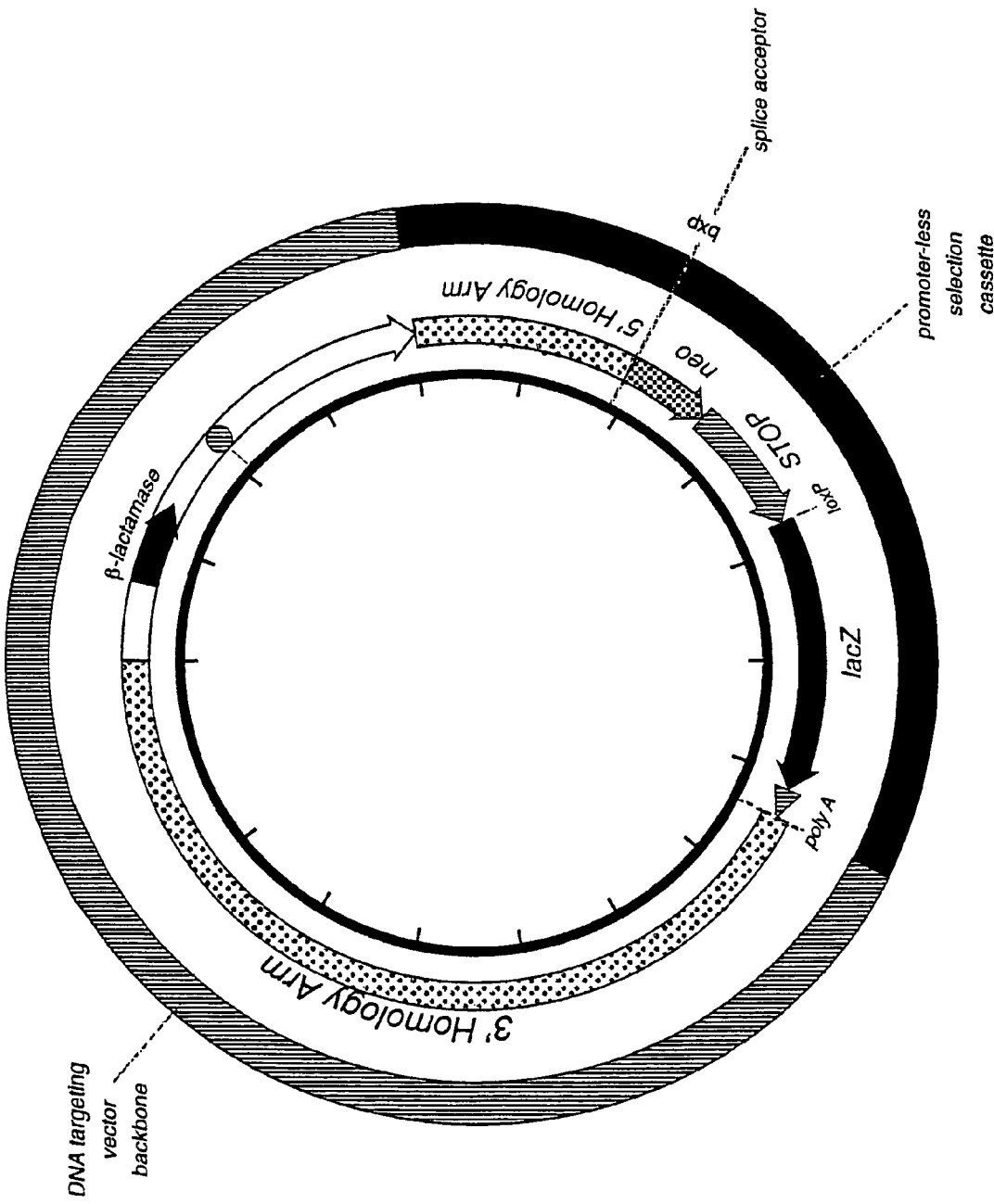
FIG. 3: A schematic representation of a typical DNA targeting vector. The vector contains a 5' homology arm which contains sequence downstream of exon 1 of the ROSA26 locus; a promoter-less selection cassette containing SA-loxP-EM7-neo4xpolyA-loxP, wherein SA is a splice acceptor sequence, the two loxP sites are the locus of recombination sites derived from bacteriophage P1, the neomycin (neo) phosphotransferase gene, and 4xpolyA which is a polyadenylation signal engineered by linking in tandem the polyadenylation signal of the murine pgk gene and three copies of a 254 bp BamHI fragment containing both early and late polyadenylation signals of Simian Virus 40 (SV40). After the second loxP site, a LacZ ORF has been engineered, followed by a human β-globin polyA. The β-globin polyA is followed by a 3' homology arm containing sequence continuous to that of the 5' homology arm.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

General

The present invention provides a method of targeting promoter-less selection cassettes into transcriptionally active loci. In particular, the invention provides a method of targeting promoter-less selection cassettes into the ROSA26 locus in eukaryotic cells, thus achieving much greater targeting efficiencies than those previously obtained with other methods and requiring considerably less effort in screening for correctly targeted events. The methods of the invention also overcome problems associated with current methodologies such as insertional inactivation of endogenous chromosomal loci and positional effects on transgene expression.

The DNA targeting vectors of the subject invention employ a selection strategy that relies on the expression of a positive drug selection marker that is driven by the endogenous promoter of the transcriptionally active locus that is being targeted. Transcriptionally active loci are loci that at the current state of differentiation of the cell are accessible to the transcriptional machinery, and the message resulting from the transcription can be found inside the cell. By targeting a transcriptionally active locus using targeting vectors that do not carry a promoter to transcribe the selection marker, only successfully targeted clones can utilize the promoter residing at the transcriptionally active locus will lead to the expression of the selectable marker gene and thus survive the selection process. A non-limiting example of a transcriptionally active locus that has been employed by Applicants in practicing the method of the invention is the ROSA26 locus. Other examples of transcriptionally active loci are the BT-5 locus (Michael et al. (1999) Mech. Dev. 85:35-47) and Oct4 (Wallace (2000) Nucleic Acids Res. 28:1455-64), each of which may be suitable for practicing the methods of the invention.

Using the ROSA26 locus as an exemplary transcriptionally active locus, Applicants have found that most, in some instances all, cells that express the selectable marker have the promoter-less selection cassette integrated into the ROSA26 locus (result shown in Table 1). Thus, employment of the methods of invention would alleviate the need to screen for targeted clones by Southern blotting or other diagnostic methods in the art. This makes possible the use of pools of targeted cells rather than individual cell clones for the generation of transgenic animals, thus eliminating the problems that are encountered when using individual clones such as the unintentional use of mutated clones to generate the chimeric animals, achieving a low degree of chimerism, and/or the lack of germlne transmission.

The present invention provides a method of gene targeting with nearly 100% efficiency, i.e. where essentially all of the drug-resistant cells that arise from selection are correctly targeted and contain a homologous recombination-mediated integration of the targeting vector. This method combines (1) targeting into a transcriptionally active locus, with (2) the use of a "promoter-less selection cassette" to effectively select for only those cells that are correctly targeted by utilizing a targeting vector that relies on the endogenous promoter of the locus being targeted for the transcription of the selectable marker gene. Additional advantages include (a) greatly reducing the need to screen for correctly targeted clones thus providing a savings of time, labor, and the associated costs and (b) reducing the probability of selecting cell clones that generate transgenic animals with a low degree of chimerism, transgenic animals that cannot contribute to the germ line, or transgenic animals that are otherwise mutated and may result in a phenotypic outcome unrelated to the expression of the transgene.

Definitions

"Eukaryotic promoter-less" means lacking a promoter that can confer expression in eukaryotic cells. "Promoter-less selection cassette" is a DNA cassette containing a selectable marker gene(s) or cDNA(s) that lacks a eukaryotic promoter. The cassette may contain other genetic elements that do not cause expression of the selectable marker gene(s) or cDNA(s) in eukaryotic cells.

"Transcriptionally active loci" are loci that at the current state of differentiation of the cell are accessible to the transcriptional machinery, and message resulting from their transcription can be found inside the cell.

A "targeting vector" is a DNA construct that contains sequences "homologous" to endogenous chromosomal nucleic acid sequences flanking a desired genetic modification(s). The flanking homology sequences, referred to as "homology arms", direct the targeting vector to a specific chromosomal location within the genome by virtue of the homology that exists between the homology arms and the corresponding endogenous sequence and introduce the desired genetic modification by a process referred to as "homologous recombination".

A "gene knock-out" is a genetic modification resulting from the disruption of the genetic information encoded in a chromosomal locus. A "gene knock-in" is a genetic modification resulting from the replacement of the genetic information encoded in a chromosomal locus with a different DNA sequence. A "knock-out organism" is an organism in which a significant proportion of the organism's cells harbor a gene knock-out. A "knock-in organism" is an organism in which a significant proportion of the organism's cells harbor a gene knock-in.

A "flanking DNA" is a segment of DNA that is contiguous with and adjacent to a particular point of reference.

Methods for Targeting a Transcriptionally Active Locus

Currently available methods for creating genetically modified mammals include pronuclear injection, or using modified ES cells. Methods employing pronuclear injection of DNA constructs or vectors containing sequences encoding a promoter, the gene of interest, a polyadenylation sequence and other regulatory or accessory elements, have been widely used but suffer from several serious drawbacks that arise primarily from the fact that the transgene is integrated randomly into the genome. Some of the methods that employ ES cells have also relied on random integration of the transgene, though more recently the idea of targeting the transgenic construct into specific chromosomal loci has also been employed. Although the latter method provides solutions to some of the problems encountered with methods where the transgene is integrated randomly, these methods still rely on gene targeting technology that gives rise to a high number of non-targeted (and therefore not useful) versus targeted ES cell clones. The methods described herein provide for gene targeting wherein virtually all the cells that express selectable marker gene and survive suitable selection arise from a correctly targeted event, thus eliminating, in most instances, the need for extensive screening of clones.

Conventional targeting vectors engineered for insertion of transgenes at selected sites (chromosomal loci) in the genome of interest consist of a 5' homology arm, followed by the transgene of interest (frequently preceded by a particular promoter), a positive selection marker gene-containing cassette, and a 3' homology arm. The selection marker gene-containing cassette used in these methods consists of a ubiquitously expressed promoter such as the phosphoglycerate kinase promoter which drives the expression of a positive drug selection gene such as neomycin phosphotransferase or other suitable drug selection gene familiar in the art, followed by a polyadenylation signal sequence to confer efficient polyadenylation of the transcribed message (FIG. 1). Since this selection cassette carries its own promoter, it confers drug resistance independent of whether it integrates at the desired (targeted) site (via homologous recombination) or at another site or sites (as a result of random/illegitimate recombination). Since integration of the cassette via homologous recombination into a target locus is a relatively rare event, many drug-resistant clones have to be screened to determine exactly which clones are correctly targeted (i.e. those clones in which the selection cassette has inserted at the chromosomal locus of choice as a result of specific homologous recombination) and which clones are not targeted (i.e. those clones in which the selection cassette has integrated randomly into the genome). Although some chromosomal loci can be targeted at a higher frequency than others, in general the screening process typically involves screening more than 100 clones by Southern blotting, PCR, or other standard methods. These processes can be tedious, time-consuming, and costly.

Several approaches have been employed to increase the frequency of targeted over non-targeted homologous recombination events or decrease the background, thus enabling easier detection of correctly targeted cells. One approach that decreases the background involves positive/negative selection, and it employs, in addition to the drug-resistance marker that can be selected for (positive selection drug resistance gene), a negative selection marker that can be selected against. An example of such a marker gene is herpes simplex virus (HSV) thymidine kinase, which can be selected against using gangcyclovir. In targeting vectors where the selection cassette employs positive/negative selection, the negative selection cassette is placed outside of the homology arms of the vector. Although there is not a large enough number of side-by-side comparisons evaluating the efficiency of targeting achieved using the same homology arms but comparing using only positive versus positive/negative selection, it has been reported that positive/negative selection increases the representation of correctly targeted clones by approximately 5 to 10 fold over that which is achieved by the corresponding targeting vector utilizing only positive selection. One of the drawbacks of positive/negative selection, and also one of the reasons why it is not 100% efficient, is that the negative selection cassette can be inactivated by mutation or, more commonly, by methylation, and therefore will not work, consequently allowing integration to occur at random sites. In addition, while it does reduce the number of clones that have to be screened, it does not completely alleviate the need for screening for correctly targeted events (Joyner, 1999, the Practical Approach Series, 293). A similar approach utilizes a passive negative selection method very similar to that just described, by replacing the negative selection marker with a gene that allows for easy visual identification of the non-targeted clones. This method suffers from similar problems as the positive/negative selection described above.

Another approach that has been used is called "exon trapping technology" which relies on engineering selection cassettes lacking a promoter. The selection cassettes typically used for exon trapping consist of a splice acceptor (SA) followed by the drug selection marker and a polyadenylation signal. When used to trap exons, this selection cassette is introduced into cells and allowed to insert randomly into the genome. Since the drug selection marker lacks its own promoter, it will only be expressed if it integrates downstream of an exon in a transcriptionally active gene. Both of these conditions (insertion within a transcriptionally active locus and insertion after an exon in that locus) must be met for the cell clone that carries the insertion to be resistant to the drug selection process. This type of selection strategy has been used to identify genes that are expressed in ES cells (Friedrich et al. (1991) Genes Dev. 5:1513-23; Wiles et al. (2000) Nat. Genet. 24:13-14). This selection strategy has not been routinely employed when engineering targeting vectors primarily because it has been considered "a method of last resort" because of the risk of selecting for differentiated ES cells. This arises if the gene is not normally expressed in undifferentiated ES cells. By selecting for drug resistance gene expression to be driven by a promoter of a locus that is not normally expressed in ES cells, one inadvertently selects for differentiated cells that express the targeted locus.

The method of the instant invention combines (1) targeting into a transcriptionally active locus, with (2) the use of a promoter-less selection cassette to effectively select for only those cells that are correctly targeted by employing a targeting vector that relies on the endogenous promoter of the locus being targeted for transcription of the drug selection gene. Because random insertion of a promoter-less drug selection marker very rarely leads to expression of that marker as result of insertion downstream of a transcriptionally active promoter, when such a cassette is directed through the use of homology arms to a specific transcriptionally active locus, essentially all of the resulting drug-resistant cells arise from homologous recombination between the targeting vector and the targeted locus. Thus, a targeting frequency of nearly 100% is obtained. In addition to having all the advantages of targeting engineered loci into a specific chromosomal locus, the novel technology described herein results in several important advances in the field of generating transgenic animals, including selecting only for correctly targeted cells, leading to nearly 100% targeting frequency, therefore alleviating the need to screen for correctly targeted cells; selecting only correctly targeted cells not only conserves time, labor, and cost, but also allows for the use of pools of drug-resistant targeted cells instead of individual cell clones for deriving transgenic animals; the use of pools of targeted cells instead of individual clones decreases the possibility that a transgenic animal is derived using a mutant clone or that chimeric animals derived from a clone will not transmit to the germ line.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for.

Many of the techniques used to construct DNA vectors described herein are standard molecular biology techniques well known to the skilled artisan (see e.g., Sambrook, J., E. F. Fritsch And T. Maniatis. Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, NY). All DNA sequencing is done by standard techniques using an ABI 373A DNA sequencer and Taq Dideoxy Terminator Cycle Sequencing Kit (Applied Biosystems, Inc., Foster City, Calif.).

Example 1

A DNA targeting vector was constructed consisting of an approximately 2 kb 5' homology arm containing sequence downstream of exon 1 of the ROSA26 locus. The ROSA26 locus encodes for an RNA that is not translated into a protein. (It should be noted that for a transcriptionally active locus where exon 1 is translated, the promoter-less selection marker should be targeted at or before exon 1 or as a fusion to the protein normally encoded by the targeted locus). The 5' homology arm extends from the NotI site to the NheI site (Friedrich et al. (1991) supra; Soriano (1999) Nat. Genet.

21:70-71). A selection cassette was inserted at that site. The selection cassette in this specific example is SA-loxP-EM7-neo4xpolyA-loxP, wherein SA is a splice acceptor sequence, the two loxP sites are the locus of recombination sites derived from bacteriophage P1 (Abremski and Hoess, 1984, J Biol Chem, 259, 1509-14), EM7 is a prokaryotic constitutively active promoter, neo is the neomycin phosphotransferase gene (Beck et al. (1982) Gene 19:3270336) and 4xpolyA is a polyadenylation signal engineered by linking in tandem the polyadenylation signal of the murine pgk gene and three copies of a 254 bp BamHI fragment containing both early and late polyadenylation signals of Simian Virus 40 (SV40). The skilled artisan will recognize that many of the individual components in the selection cassette can be substituted with comparable or equivalent components. For example, the 5' homology arm could start anywhere within the Rosa26 gene as long as it placed downstream of the transcription start site, the loxP recombination sites can be substituted with FRT or other sites recognized by recombinases, the EM7 promoter can be substituted with any bacterial promoter that is silent in mammalian cells, and the neo gene can be substituted with any suitable selectable marker gene that can be selected for both in bacteria and in mammalian cells. After the second loxP site, an open reading frame (ORF) encoding for LacZ has been engineered followed by a β-globin polyadenylation signal (β-globin polyA) of the rabbit β-globin gene (Accession K03256 or M12603). Any ORF can be placed here in place of LacZ, depending on the desired result, and that other polyadenylation signals can be used in place of the β-globin polyA. The β-globin polyA is followed by a 3' homology arm containing sequence that is continuous with the 5' homology arm in the native ROSA26 locus. The 3' homology arm extends approximately 9.4 kb past the site of insertion of the selection cassette and contains ROSA26 sequence up to the unique EcoRI site. The choice of what segment and how much of the locus sequence to include in the homology arm generally needs to be empirically determined, and can be determined without undue experimentation. However, care should be taken not to include the promoter of the locus being targeted as part of the homology arms, as doing so would counteract the selection strategy. Note the absence of a mammalian promoter in the selection cassette and the use of a prokaryotic promoter, EM7. The EM7 promoter is silent in mammalian cells but can be used to drive neo expression in bacteria and thus confer the host *E. coli* with kanamycin resistance. In addition, this targeting vector contains an origin of replication and a β-lactamase gene, used to confer ampicillin resistance in host bacteria. Since the selection marker contained in this targeting vector lacks a mammalian promoter, the only way that this targeting vector can confer drug resistance to mammalian cells is if the selection marker integrates in appropriate fashion within a gene that is expressed in the target cell. The likelihood of this happening randomly is rather low since each cell type only transcribes a subset of all the genes in a genome. Thus, by including the 5' and 3' homology arms derived from the ROSA26 locus, Applicants are effectively and efficiently biasing for proper insertion of the targeting vector into the target locus. Subsequent to construction, the DNA targeting vector was introduced into ES cells by standard methods familiar in the art and the percentage of targeting events was determined. Briefly, the targeting vector was linearized after the 3' end of the 3' homology arm by restriction enzyme digestion and transfected into ES cells employing standard methodology and in the case of Neo$^r$, G418-resistant clones were selected, again by standard methods familiar in the art. Individual clones were picked and analyzed by standard Southern blotting to determine which clones were targeted. All clones examined were found to be correctly targeted.

In the case of the floxed promoter-less Neo cassette followed by LacZ, expression of LacZ is absent until the floxed promoter-less Neo cassette is removed using Cre recombinase. After excision of this cassette, a single LoxP site remains followed by LacZ. Since there no long exists a transcriptional stop signal between the promoter of the targeted locus and LacZ, then expression of LacZ is achieved. Therefore, this embodiment of this method not only provides for vastly improved targeting efficiency but also retains the versatility associated with previously described methods for regulating transgene expression through the use of site-specific recombinases and their cognate sites.

To demonstrate the reproducibility and general applicability of the methods of the invention, equivalent DNA targeting vectors were constructed using the ORF cDNAs encoding for other genes (these genes essentially replaced lacZ in the vector described supra). Table 1 lists the targeting frequencies obtained using these DNA targeting vectors. Note that in the targeting vectors only the gene of interest is replaced. In these examples, the selection marker and other features of the DNA targeting vector remain the same.

TABLE 1

| transgene | Number of G418-resistant clones screened | Targeting Frequency |
| --- | --- | --- |
| (neo) | 8 | 100% (8/8) |
| hROR1 | 20 | 100% (20/20) |
| CMVp-lacZ | 14 | 100% (14/14) |
| hROR2 | 6 | 100% (6/6) |
| α1p-OGH | 7 | 100% (7/7) |
| SM22a-lacZ | 5 | 100% (5/5) |
| m(HTKL)2-Fc | 10 | 100% (10/10) |
| mMdk2-Fc | 8 | 100% (8/8) |
| SM22a-lacZ | 5 | 100% (5/5) |

We claim:

1. A method of targeting a selection cassette into a transcriptionally active gene in a mouse embryonic stem (ES) cell, comprising:
   (a) constructing a DNA targeting vector consisting of, in order, (1) a 5' homology arm, (2) a promoterless selection cassette comprising, in order, a splice acceptor sequence, a selectable marker gene and a first polyadenylation signal sequence, wherein the selectable marker gene and first polyadenylation signal sequence are flanked on each side by a site-specific recombinase recognition sequence, (3) a gene of interest and a second polyadenylation signal sequence, and (4) a 3' homology arm, wherein the 5' and 3' homology arms each display homology to a sequence of the transcriptionally active gene, and wherein upon homologous recombination the promoterless selectable marker gene is operably linked to the promoter of the transcriptionally active gene, and the gene of interest is operably linked to the promoter of the transcriptionally active gene following recombinase-mediated removal of the selectable marker;
   (b) introducing the DNA targeting vector of (a) into the ES cell;
   (c) selecting the ES cell of (b) for expression of the selectable marker gene, and
   (d) screening the selected ES cells of (c) to identify those cells in which the selection cassette has integrated into the transcriptionally active gene, wherein targeting frequency is 100%.

2. The method of claim 1, wherein the orientation of the site-specific recombinase recognition sequence flanking each side of the selectable marker gene and first polyadenylation signal sequence is the same.

3. The method of claim 1, wherein the site-specific recombinase recognition sequences are LoxP sites.

4. The method of claim 1, wherein the transcriptionally active gene is ROSA26.

5. The method of claim 4, wherein the orientation of the site-specific recombinase recognition sequence flanking each side of the selectable marker gene and first polyadenylation signal sequence is the same.

6. The method of claim 4, wherein the site-specific recombinase recognition sequences are LoxP sites.

7. A method of expressing a gene of interest in a mouse embryonic stem (ES) cell, comprising:
  (a) targeting a DNA construct into a transcriptionally active gene in a genome of a mouse ES cell, wherein the DNA construct consists of, in order, (1) a 5' homology arm; (2) a promoterless selection cassette, wherein the promoterless selection cassette comprises, in order, a first site-specific recombinase recognition site sequence, a splice acceptor sequence, a selectable marker gene, a first polyadenylation signal sequence, and a second site-specific recombinase recognition sequence; (3) the gene of interest and a second polyadenylation signal sequence; and (4) a 3' homology arm, wherein the 5' and 3' homology arms each display homology to a sequence of the transcriptionally active gene; wherein upon homologous recombination the promoterless selection cassette is operably linked to a promoter of the transcriptionally active gene;
  (b) introducing the site-specific recombinase into the ES cell, wherein the site-specific recombinase removes the promoterless selection cassette and operably links the gene of interest to the promoter of the transcriptionally active gene; and
  (c) expressing the gene of interest in the mouse ES cell, wherein targeting frequency of the DNA construct is 100%.

8. The method of claim 7, further comprising a step of selecting the ES cell for expression of the selectable marker gene before introducing the site-specific recombinase into the ES cell.

* * * * *